United States Patent [19] [11] 4,113,714
Garsky et al. [45] Sep. 12, 1978

[54] [DES-ALA¹, GLY²-DESAMINO-CYS³]SOMATOSTATIN

[75] Inventors: Victor M. Garsky, Havertown; William H. McGregor, Malvern, both of Pa.

[73] Assignee: American Home Products Corporation, New York, N.Y.

[21] Appl. No.: 538,628

[22] Filed: Jan. 3, 1975

[51] Int. Cl.² ............ C07C 103/52; A61K 37/00
[52] U.S. Cl. ............ 260/112.5 S; 424/177
[58] Field of Search ............ 260/112.5 S

[56] References Cited
U.S. PATENT DOCUMENTS

| 3,842,066 | 10/1974 | McKinley et al. | 260/112.5 R |
| 3,842,067 | 10/1974 | Sarantakis | 260/112.5 R |
| 3,882,098 | 5/1975 | Sarantakis | 260/112.5 R |
| 3,904,594 | 9/1975 | Guillemin et al. | 260/112.5 R |

OTHER PUBLICATIONS

Berde et al., "Neurohypophysical Hormones and Similar Polypeptides, ", Handbook of Experimental Pharmacology, vol. 23, Springer–Verlag, Berlin, 1968, pp. 842–845, 856–857, 862.

Primary Examiner—Delbert R. Phillips
Attorney, Agent, or Firm—Richard K. Jackson

[57] ABSTRACT

The growth hormone release inhibiting undecapeptide of the formula

Nα-(3-mercaptopropionyl)-L-Lys-L-Asn-L-Phe-L-Phe-L-Trp-L-Lys-L-Thr-L-Phe-L-Thr-L-Ser-L-Cys cyclic (1–11) disulfide.

2 Claims, No Drawings

[DES-ALA¹, GLY²-DESAMINO-CYS³]SOMATOSTATIN

BACKGROUND OF THE INVENTION

It is known that crude hypothalamic preparations will inhibit the secretion of the growth hormone, somatotropin. Recently, the structure of a somatotropin-release-inhibiting-factor (SRIF) has been elucidated by Brazeau et al., Science, 179, 77(1973) as

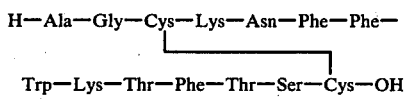

This tetradecapeptide is commonly referred to as somatostatin.

DESCRIPTION OF THE INVENTION

In accordance with this invention, there is provided an undecapeptide (des-Ala'-Gly²-desamino-Cys³-SRIF) of the formula:

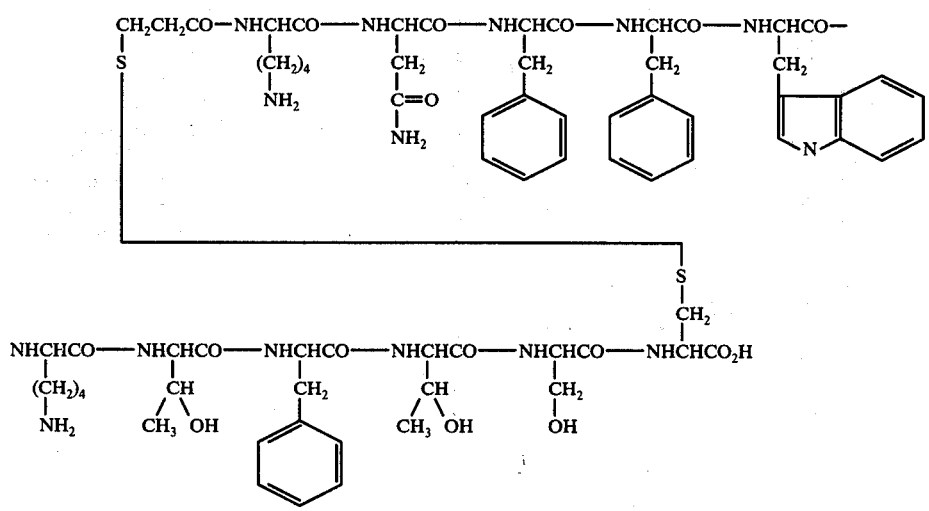

which may also be depicted as:

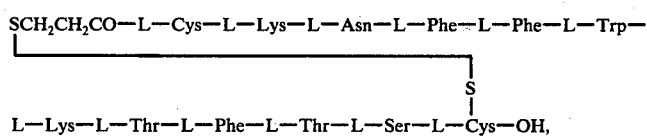

or named:
N$^\alpha$-(3-mercaptopropionyl)-L-Lys-L-Asn-L-Phe-L-Phe-L-Trp-L-Lys-L-Thr-L-Phe-L-Thr-L-Ser-L-Cys cyclic (1-11) disulfide.

The undecapeptide of this invention inhibits the release of growth hormone (GH) from the pituitary in warm-blooded animals and is useful in the treatment of diseases of human and non-human animals resulting from excessive growth hormone secretion, such as juvenile diabetes and acromegaly, the undecapeptide is administered to the patient under the guidance of a physician, orally or parenterally, in an amount dictated by the extent of the dysfunction as determined by the physician. The compound may be administered alone or in conjunction with conventional pharmaceutically acceptable carriers and adjuvants, at a dosage of from about 0.2 to 10 milligrams per kilogram host body weight.

The activity of the undecapeptide of this invention was established in both in vitro and in vivo testing procedures, employing modifications of the techniques disclosed by Penso et al., Tissue Culture in Biological Research, Elsevier, 1963, p. 98; Berson et al., Metabolism, 13, 1135(1964).

The in vitro tests were conducted by covering cultured rat pituitary cells contained in petri dishes with five milliliter portions of the undecapeptide, as its diacetate salt, in Eagles medium for three hours at 37° C. Three Petri dishes were employed for each solution concentration. The amount of growth hormone produced by the cultured pituitary cells is then compared with growth hormone produced by non-treated cells prepared in identical manner, via growth hormone radioimmunoassay. The difference between the growth hormone produced by treated and non-treated pituitary cells establishes the amount of inhibition by the compound under study.

The cultured pituitary cells are prepared by excising and mincing rat pituitary glands followed by enzymatic separation of the cells (collagenase and hyaluronidase) and culture on synthetic nutrient media. When the cells attach themselves to the bottom of the plastic petri dish and cover the nutrient surface, they are washed with Eagles medium containing only inorganic salts, glucose and antibiotics in which state they are ready for use as above described.

The in vivo activity tests were conducted by injecting Nembutal into male rats weighing 200 to 240 grams. Five minutes after the injection, the undecapeptide, as its diacetate salt, (500 ug) in 80 percent polyethylene glycol (PEG 400) and water (1 milliliter) was administered subcutaneously by injection. Control rats were injected with 80 percent polyethylene glycol (PEG 400) alone. After fifteen minutes, the rats were sacrificed and their blood plasmas assayed for growth hormone by radio-immunoassay.

The activity of the undecapeptide of this invention was compared in vitro with somatostatin with the following results in which the concentration valves given are in nanograms/milliliter:

| Compound | Concentration ng/ml | Growth Hormone Secreted ng/ml |
| --- | --- | --- |
| control | none | 441±12 |
| somatostatin | 100 | 250±13 |
| somatostatin | 50 | 271±22 |
| somatostatin | 10 | 260±8 |
| des-Ala-Gly-des-amino-Cys-SRIF-diacetate | 1000 | 312±23 |
| | 100 | 321±16 |
| | 10 | 346±25 |
| | 1 | 320±30 |

The undecapeptide of this invention reduces the growth hormone concentration in blood plasma markedly when administered to the standard test animal (the rat) in comparison to the control animals. Thus, the average growth hormone concentration per milliliter of plasma in seven rats treated subcutaneously with 500 ug of the undecapeptide was 63.3 ± 8.8 × $10^{-9}$ grams whereas the control animals plasma, based on an average of eight rats, contained 176.8 ± 28 × $10^{-9}$ grams growth hormone per milliliter (p = <0.05).

In the following preparatory scheme, the abbreviation "t-Boc" refers to the tertiary butyloxycarbonyl protecting group. The undecapeptide synthesis was conducted by solid phase methodology (Merrifield, J.A.C.S. 85, 2149(1964)).

EXAMPLE
$N^\alpha$-(3-Mercaptopropionyl)-L-Lysyl-L-Asparginyl-L-Phenylalanyl-L-Phenylalanyl-L-Tryptophyl-L-Lysyl-L-Theronyl-L-Phenylalanyl-L-Threonyl-L-Seryl-L-Cysteinyl Cyclic (1-11) Disulfide Chloromethylated polystyrene resin (25 g., 0.75 m moles Cl/g) is heated (80° C.) in a 500 ml round bottom flask with t-butyloxycarbonyl S-p-methoxybenzyl-L-cysteine (15.9 g., 47 m moles), and potassium tertiary-butyl alcoholate (4.7 g., 42 m moles) in dimethyl sulfoxide (150 ml), for 4 hours. The resin is filtered and washed on the filter with ethanol, methylene chloride, 15% triethylamine in methylene chloride, dimethylformamide, methylene chloride and methanol (three times each). The resin was determined to be substituted to the extent of 0.57 m moles of cysteine per gram of resin.

A portion of the resin (3.0 g.) is transferred to a reaction vessel of a Beckman 990 peptide synthesizer, deprotected and neutralized as follows: the resin is treated with two portions of 1:1 trifluoroacetic acid and methylene chloride containing 5% ethanedithiol. This treatment consists of a 5 minute prewash and a 30 minute deprotection. The peptide resin is then washed with methylene chloride (six times), 15% triethylamine in dimethylformamide (three times) and methylene chloride (six times). Three minutes was allowed for each wash. After deprotection of the peptide resin the following amino acid residues are introduced consecutively: t-Boc-O-benzyl-L-serine, t-Boc-O-benzyl-L-threonine, t-Boc-L-phenylalanine, t-Boc-O-benzyl threonine, t-Boc-$N^\epsilon$-(2-chlorobenzyloxycarbonyl)-L-lysine, t-Boc-L-tryptophan, t-Boc-L-phenylalanine, t-Boc-L-phenylalanine, t-Boc-L-asparagine-p-nitrophenyl ester, t-Boc-$N^\epsilon$-(2-chlorobenzyloxycarbonyl)-L-lysine. All couplings are carried out once in methylene chloride using 6 equivalents of protected amino acid each time and a 10% excess of diisopropylcarbodiimide as a coupling reagent (diisopropylcarbodiimide added in two portions over 30 minutes) allowing 5 hours for each coupling. Asparagine, the only exception, is coupled twice as the p-nitro-phenyl ester (in dimethylformamide with a catalytic amount of acetic acid) allowing 10 hours for each coupling. Following the coupling of each amino acid residue the peptide resin is acetylated with 2.5% acetylimidazole in methylene chloride for 30 minutes. At the end of the final coupling and wash the peptide resin is dried under vacuum to yield 6.0 of peptide resin.

A portion of the above resin (3.0 g., 0.85 m moles) is coupled twice with S-trityl-3-mercaptopropionic acid for 18 hours by the method described above for coupling the amino acids other than asparagine.

The above described preparation is treated in vacuo with anhydrous liquid hydrogen fluoride (80 ml) and anisole (10 ml) at 0° C. for 45 minutes. The hydrogen fluoride and anisole are removed under reduced pressure and the residue suspended in 50% acetic acid (30 ml). This slurry is then diluted with water (3 liters) and the pH adjusted to 7.5 with ammonium hydroxide. After 24 hours the solution is filtered from the resin and the filtrate lyophilyzed to leave the above titled crude product (4.0 g.).

The above titled crude produce is purified as follows: 4.0 g. of this product is suspended in 50% acetic acid (15 ml) and centrifuged. A portion (5 ml) of the supernatant liquid is applied to a column (2.9 cm in diameter and 150 cm in height) with a bed of Sephadex G-25 medium in 50% acetic acid. The column is eluted with 50% acetic acid and 2 ml fractions collected. Tubes 125-130 are shown to be homogeneous by thin layer chromatography systems 4:1:5 (n-butanol: acetic acid: water) $R_f$ 0.64, and 7:7:6 (isoamyl alcohol:pyridine:water) $R_f$ 0.67, on cellulose. Thin layer chromatograms are visualized with iodine and chlorine peptide reagent. The product is recovered as the diacetate salt.

After hydrolysis of the peptide for 24 hours in methanesulfonic acid at 100° C. in an evacuated sealed tube, the following values for the product are obtained: Lys 1.00, Asp 1.01, Phe 0.99, Thr 0.87, Ser 0.64, Cys 0.81, Trp 0.74.

What is claimed is:

1. The compound $N^\alpha$-(3-mercaptopropionyl)-L-Lys-L-Asn-L-Phe-L-Phe-L-Trp-L-Lys-L-Thr-L-Phe-L-Thr-L-Ser-L-Cys cyclic (1-11) disulfide and pharmaceutically acceptable salts thereof.

2. The peptide having the structure

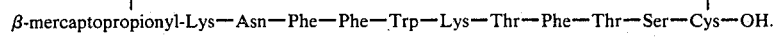

β-mercaptopropionyl-Lys—Asn—Phe—Phe—Trp—Lys—Thr—Phe—Thr—Ser—Cys—OH.